United States Patent [19]
Chen et al.

[11] Patent Number: 6,013,848
[45] Date of Patent: Jan. 11, 2000

[54] CONVERSION OF HEAVY POLYALKYLAROMATIC COMPOUNDS

[75] Inventors: Jamin Chen, Montville; Chuen Y. Yeh, Edison, both of N.J.

[73] Assignee: Catalytic Distillation Technologies

[21] Appl. No.: 08/889,729

[22] Filed: Jul. 8, 1997

[51] Int. Cl.[7] ............................ C07C 1/00; C07C 2/64; C07C 2/68; C07C 5/22
[52] U.S. Cl. .................... 585/323; 585/449; 585/450; 585/467; 585/475
[58] Field of Search ................... 585/323, 449, 585/450, 467, 475

[56] References Cited

U.S. PATENT DOCUMENTS

| | | | |
|---|---|---|---|
| 3,957,621 | 5/1976 | Bonacci et al. | 208/60 |
| 4,127,471 | 11/1978 | Suggitt et al. | 208/60 |
| 4,169,111 | 9/1979 | Wight | 585/323 |
| 4,857,666 | 8/1989 | Barger et al. | 585/323 |
| 5,003,119 | 3/1991 | Sardina et al. | 585/323 |
| 5,081,323 | 1/1992 | Innes et al. | 585/449 |
| 5,196,623 | 3/1993 | Butler | 585/467 |
| 5,243,115 | 9/1993 | Smith, Jr. et al. | 585/446 |
| 5,476,978 | 12/1995 | Smith, Jr. et al. | 585/323 |

*Primary Examiner*—Walter D. Griffin
*Assistant Examiner*—Thuan D. Dang
*Attorney, Agent, or Firm*—Kenneth H. Johnson

[57] ABSTRACT

A process for the conversion of heavy bottoms from aromatic alkylation known as "flux oil" and containing heavier polyalkylaromatic compounds, in which the heavier polyalkylates are fed along with aromatic to a reactor containing an acidic zeolite catalyst for conversion to light mono-, and poly alkylaromatic compounds. The light polyalkylates may then be transalkylated with benzene to form additional monoalkylate.

17 Claims, 1 Drawing Sheet

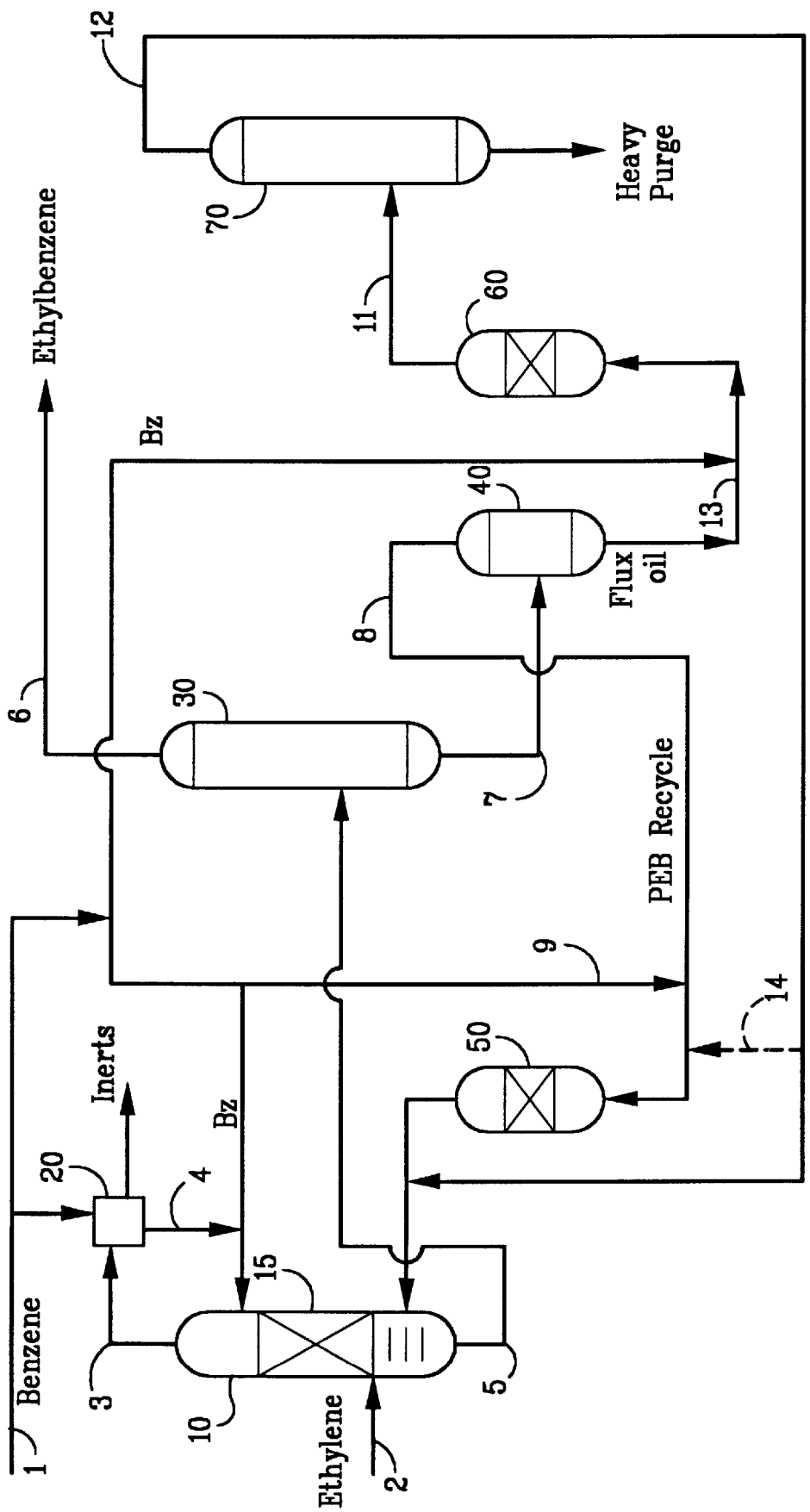

CONVERSION OF HEAVY POLYALKYLAROMATIC COMPOUNDS

BACKGROUND OF THE INVENTION

1. Field of the Invention

The present invention relates to a process for the recovery of valuable monoalkylates from high boiling residue (flux oil) of aromatic alkylation processes, thereby improving the yield of monoalkylates in an aromatic alkylation process. More particularly the invention relates to a process for converting the heavier polyalkylates of the flux oil to monoalkylates and lighter polyalkylates.

2. Related Art

Aromatic alkylation processes are used to prepare various useful alkylated derivatives of benzene and naphthalene. For example, dodecylbenzene, a useful precursor for the surfactant industry may be prepared by the alkylation of benzene with dodecene in the presence of a suitable catalyst. Other examples include the alkylation of benzene with ethylene or propylene to yield ethylbenzene or cumene respectively. Ethylbenzene may be converted to styrene, and cumene is useful in the production of phenol and acetone.

In aromatic alkylation processes it is generally difficult to control the product distribution and one normally obtains an appreciable amount of polyalkylates. Since the products of the monoalkylation are more valuable, the di, tri, and tetra-alkylates may be separated from the monoalkylates and then transalkylated to produce more of the monoalkylate. See for examples, U.S. Pat. Nos. 5,055,627 and 5,243,115. The general practice has been to discard the heavier polyalkylates (flux oil) to fuel oil.

It is an advantage of the present invention to convert at least a portion of the heavier polyalkylates to lighter polyalkylates which can be more readily transalkylated to the monoalkylate.

SUMMARY OF THE INVENTION

The heavy polyalkylates from a distillation column which separates lighter polyalkylates from the heavier polyalkylates is called flux oil. The present invention is an improvement in the alkylation of aromatic compounds with olefins comprising reacting an olefin with an aromatic compound to produce a reaction mixture of mono- and poly-alkylated aromatic compounds, separating monoalkyl aromatic compound and a first mixture of polyalkylated compounds mixture having a first boiling range point and recovering a second mixture of poly-alkylaromatic compounds, flux oil, having a second boiling point range greater than said first boiling point range wherein the improvement comprises reacting said second mixture of polyalkyl aromatic compounds and said aromatic compound in the presence of a transalkylation catalyst under transalkylation conditions to produce monoalkyl aromatic compound and a third mixture of polyalkyl aromatic compounds having said first boiling point range. This flux oil is preferably fed to a reactor containing acidic zeolite molecular sieve catalyst along with a very high ratio of benzene to flux oil ratio and thus transalkylate the polyalkylates contained in the flux oil to monoalkylate, and the light di-, tri or tetra-alkylates corresponding to the those separated from the flux oil in the alkylation reaction. The monoalkylate is recovered and the light polyalkylates may then be fed to a transalkylator for further monoalkylate production.

Thus according to the present process the relatively useless flux oil polyalkylates are converted to the desirable monoalkylate which is separated and recovered and into the light polyalkylates that are useful for transalkylation into the monoalkylate.

BRIEF DESCRIPTION OF THE DRAWING

The figure is a flow diagram in schematic form of the use of the present process in an ethylbenzene process.

DETAILED DESCRIPTION OF THE INVENTION

While any catalyst that is suitable for the transalkylation reaction is usable, the preferred catalysts for the process are the acidic molecular sieves. Molecular sieves are porous crystalline, three-dimensional alumina-silicates of the zeolite mineral group. The crystal skeleton is composed of silicon and aluminum atoms each surrounded by four oxygen atoms to form a small pyramid or tetrahedron (tetrahedral coordination). The term molecular sieve can be applied to both naturally occurring zeolites and synthetic zeolites. Naturally occurring zeolites have irregular pore size and are not generally considered as equivalent to synthetic zeolites. In the present invention, however, naturally occurring zeolites are acceptable so long as they are substantially pure. The balance of the present discussion shall be directed to the synthetic zeolites with the understanding that natural zeolites are considered equivalent thereto as indicated above, i.e., insofar as the natural zeolites are the functional equivalents to the synthetic zeolites.

Usually synthetic zeolites are prepared in the sodium form, that is, with a sodium cation in close proximity to each aluminum tetrahedron and balancing its charge. To date several types of molecular sieves have been reported, A, X, Y and L erionite, omega, beta and mordenite. The A types have relative small pore size. By the term pore size is meant the effective pore size (diameter) rather than the free pore size (diameter). Types X and Y have larger pore size and differ as to the range of ratio of $Al_2O_3$ to $SiO_2$ as:

Type X --- $Al_2O_3/2.0–3.0\ SiO_2$

Type Y --- $Al_2O_3/3.0–6.0\ SiO_2$

Type L, beta and other types listed have still higher ratios of $SiO_2$ to $Al_2O_3$.

The mole sieve catalysts employed in the present invention are the acid form mole sieves or exhibit acidic characteristics. The acid form of the mole sieves is commercially available, but also may be prepared by treating the mole sieves with acid to exchange Na for hydrogen. Another method to produce the acid form is to treat the mole sieve with decomposable cations (generally ammonium ions) to replace Na with the decomposable ions and thereafter to heat the mole sieve to decompose the cation leaving the acid form. Generally the Na form mole sieve is treated with soluble ammonium salts to exchange the Na and thereafter the mole sieve is heated to a temperature of about ~550° C. to remove the ammonia. The exchange of $Na^+$ ions with $NH^+_4$ is more easily carried out than with multivalent ions as described below and these catalysts are generally more active but less stable to heat than the multivalent cation exchange forms. Mole sieves, which have had their alkali metal reduced to low levels by partial treatment with $NH^+_4$ and partial multivalent metal cation exchange, possess increased activity and increased stability.

In addition to mole sieves which are acidic according to the Brönsted Theory, those mole sieves which exhibit acidic characteristics under the Lewis Theory, for example, calcium exchanged mole sieves, are suitable for the present reaction. By exchanging the univalent cations (e.g. $Na^+$)

with multivalent cation, strong ionic activity is imparted. The ratio of $SiO_2:Al_2O_3$, valence and radius of the cation and the extent of exchange all affect the catalyst activity. In general, activity increases with (1) increased $SiO_2:Al_2O_3$ ratio, (2) decreased cation radius and an increase in cation valence. The effect of replacing univalent ions (e.g. $Na^+$) with bivalent (e.g. $Ca^{++}$) is much greater than replacing the bivalent ions with cations of greater valence.

The various types of mole sieves having reduced alkali metal content are characterized as the acid form molecular sieve and are all contemplated as useful in the present invention. The acid form mole sieves are generally produced and available as particles in the range of <10 micron (powders) to 0.2 inch in diameter (beads).

The olefins may be $C_2$ to $C_{20}$ olefins, preferably $C_2$ to $C_{12}$ olefins, including normal and branched forms thereof. For example, suitable olefins are ethylene, propylene, butylene, isobutylene, 1-pentene, 1-hexene, 2-hexene, 2,3-dimethyl-1-pentene, 1-octene, diisobutylene, 1-nonene and 1-decene, dodecene and the like. The olefins may contain substituents which do not interfere with the alkylation. In one preferred embodiment the olefin is a $C_2$ to $C_4$ olefin.

The organic aromatic compounds are preferably those having a boiling point of 250° C. or less under the pressure conditions of the reactor. The organic aromatic compounds include hydrocarbons of one or more rings and 6 to 20 carbon atoms which may contain substituents which do not interfere with the alkylation including halogen (Cl, Br, F and I), OH and alkyl, cycloalkyl, aralkyl and alkaryl radicals of 1 to 10 carbon atoms. Suitable organic, aromatic compounds include benzene, xylene, toluene, phenol, cresol, ethyl benzene, diethyl benzene, naphthalene, indene, phenyl bromide, 1-bromo-2-chloro-benzene, 1-bromo-4-cyclohexyl benzene, 2-bromo-1,4-dihydroxy-benzene, 1(bromomethyl) naphthalene, 1,2-dihydronaphthalene and the like, a preferred group of compounds for use in the present process is benzene, xylene, toluene, phenol, and cresol.

The molar ratio of organic aromatic compound to olefin in the alkylation may be in the range of 2:1 to 100:1, preferably 2:1 to 50:1 and more desirably about 2:1 to 10:1. The greater the excess of organic aromatic compound, the more the selectivity to the monosubstituted product is improved. The weight ratio of aromatic compound to said heavy polyalkylate containing stream is preferably between 25:1 and 50:1 in the transalkylation.

The heavy polyalkylates are typically the bottoms from a distillation separating light polyalkylates from the heavier polyalkylates such as in a polyethylbenzene (PEB) column in an ethylbenzene plant. As shown in the figure, benzene is fed to a distillation column reactor 10 via flow line 1 through the reflux drum 20. Ethylene is fed into the distillation column reactor below the catalyst bed 15 via flow line 2. In the distillation column reactor the benzene reacts with the ethylene to produce ethylbenzene and the polyalkylates. The unreacted benzene is removed as overheads via flow line 3 and recycled to the reactor as reflux via flow line 4. The alkylated products removed as bottoms via flow line 5 and passed to the primary ethylbenzene column 30 where the ethylbenzene is taken as overheads via flow line 6 with the polyalkylated products being removed as bottoms via flow line 7. The bottoms from the ethylbenzene column 30 are then passed on to the PEB column 40.

The PEB column separates the lighter polyethylbenzenes as overheads in flow line 8 from the heavier materials. The light polyethylbenzenes are then usually fed to a transalkylation unit 50 along with additional benzene from flow line 9 to produce additional monoalkylate. The catalyst for the transalkylation reaction is usually the same type as used for the alkylation reaction, typically a zeolite.

The column could also be in a cumene plant and would then be separating light polypropylbenzenes from the heavier material. As in the ethylbenzene plant the light polypropylbenzenes would be fed to a transalkylation reactor along with additional benzene to produce additional cumene.

The bottoms from column 40 is called flux oil and heretofore has simply been used as fuel oil. The bottoms from the PEB column in an ethylbenzene plant typically contain 1,1 di-phenyl ethane (DPE), bibenzyl (BB) or 1,2-diphenyl ethane, penta-ethylbenzene, phenyl-ethylphenylethanes (PEPE), hexaethyl-benzene (HEB) and diethyl-phenylethane (DEPE). These are by-products and their formation represents a yield loss.

In the present invention the flux oil in flow line 13 is admixed with excess benzene and then fed to a reactor 60 containing additional zeolite catalyst and reacted at from about 190–230° C. and autogeneous pressure to form additional monoalkylate or lower polyalkylates such as di and triethyl benzene. The effluent is then routed via flow line 11 to a distillation column 70 to recover the benzene, monoalkylate and di-tri and tetra ethyl benzenes from overhead which is sent to the distillation column reactor 10 via line 12. A portion may be sent directly to the transalkylation reactor 50 via flow line 14. The bottoms from the last distillation column reactor is then sent to fuel oil.

EXAMPLES 1 and 2

These examples illustrate typical components of flux oil as obtained from a PEB column. Table I below shows the GC analysis for the products from each run.

TABLE I

| | Example | |
|---|---|---|
| Composition, wt %* | 1 | 2 |
| Benzene | 1.65 | 0.03 |
| Ethylbenzene | 0.07 | 0.05 |
| Diethylbenzene | 0.10 | 0.16 |
| Triethylbenzene | 0.02 | 3.71 |
| Tetraethylbenzene | 30.51 | 7.45 |
| DPE | 19.83 | 8.31 |
| BB | 0.53 | 0.24 |
| Pentaethylbenzene | 14.53 | 12.03 |
| PEPE1 | 8.28 | 16.79 |
| PEPE2 | 2.63 | 14.85 |
| HEB | 2.72 | 9.60 |
| DEPE | 0.68 | 1.76 |

*Only the major and known components are shown; does not = 100%.

The heavy polyalkylates are considered those heavier than the tetraethylbenzene.

EXAMPLE 3

A mixture of 98.4 parts by weight benzene and 1.6 parts by weight of the flux oil from Example 1 was passed through a fixed bed reactor containing 15 grams zeolite Y catalyst at 200° C. at a feed rate of 2.5 grams/minunte [weight hour space velocity (WHSV)=10 $hr^{-1}$]. The reaction was carried out in a 1.00"(o.d.)×10" fixed bed reactor containing 15 grams of zeolite Y catalyst at 200° C. The feed rate was 2.5 g/min. Both the feed and resulting product were analyzed by gas chromatography to determine the composition. The results are summarized in Table II below. As can be seen there was a significant reduction in all heavier components except DPE. It was also noted that components of ethylbenzene, diethylbenzene and triethylbenzene were all produced. The net reduction in heavies was approximately 55–60%.

TABLE II

| Composition, wt %* | Feed | Product | % Change |
|---|---|---|---|
| Benzene | 98.3830 | 97.5115 | −0.9 |
| Ethylbenzene | 0.0037 | 1.3428 | +36192 |
| Diethylbenzene | 0.0003 | 0.0757 | +25133 |
| Triethylbenzene | 0.0000 | 0.0883 | NA |
| Tetraethylbenzene | 0.5059 | 0.1406 | −72 |
| DPE | 0.3053 | 0.3602 | +18 |
| BB | 0.0051 | 0.0033 | −35 |
| Pentaethylbenzene | 0.2475 | 0.0077 | −97 |
| PEPE1 | 0.1184 | 0.0068 | −94 |
| PEPE2 | 0.0056 | 0.0052 | −7 |
| HEB | 0.0387 | 0.0026 | −93 |
| DEPE | 0.0086 | 0.0000 | −100 |

*Only the major and known components are shown; does not = 100%

EXAMPLE 4

A mixture of 95.7 parts by weight benzene and 4.3 parts by weight of the flux oil from Example 2 was passed through a fixed bed reactor containing 15 grams zeolite Y catalyst at 200° C. at a feed rate of 2.5 gr/min [weight hour space velocity (WHSV)=10 hr$^{-1}$]. Both the feed and resulting product were analyzed by gas chromatography to determine the composition. The results are summarized in Table III below. Again there was a significant reduction in all heavier components except DPE. It was also noted that components of ethylbenzene, diethylbenzene and triethylbenzene were all produced. The net reduction in heavies was approximately 20%.

TABLE III

| Composition, wt %* | Feed | Product | % Change |
|---|---|---|---|
| Benzene | 95.7164 | 93.8984 | −1.9 |
| Ethylbenzene | 0.0035 | 1.9010 | +54214 |
| Diethylbenzene | 0.0094 | 0.3343 | +3456 |
| Triethylbenzene | 0.1094 | 0.1158 | +6 |
| Tetraethylbenzene | 0.3464 | 0.3100 | −11 |
| DPE | 0.3600 | 1.3726 | +337 |
| BB | 0.0113 | 0.0138 | +22 |
| Pentaethylbenzene | 0.5185 | 0.2469 | −52 |
| PEPE1 | 0.6582 | 0.1281 | −81 |
| PEPE2 | 0.3335 | 0.0312 | −91 |
| HEB | 0.4016 | 0.908 | −77 |
| DEPE | 0.1025 | 0.0676 | −34 |

*Only the major and known components are shown; does not = 100%

The invention claimed is:

1. In a process for the alkylation of benzene with ethylene comprising reacting ethylene with an benzene to produce a reaction mixture of ethyl benzene and poly-alkylated benzene, separating ethyl benzene and a light polyethyl benzene mixture containing tetraethyl benzene and lighter polyalkylated aromatic compounds, and recovering a heavy polyalkylated aromatic compound mixture, containing polyalkylated aromatic compounds heavier than tetraethyl benzene wherein the improvement comprises reacting said heavy polyalkylated aromatic compound mixture with said benzene in the presence of a transalkylation catalyst under transalkylation conditions to produce ethyl benzene and a polyalkylated aromatic compound mixture containing tetraethyl benzene and lighter polyalkylated aromatic compounds.

2. The process according to claim 1 wherein said transalkylation catalyst comprises acidic zeolite.

3. The process according to claim 2 wherein the acidic zeolite comprises a Y zeolite.

4. The process according to claim 1 wherein the weight ratio of said benzene to said heavy polyalkylated aromatic compound containing stream is between 2:1 to 100:1.

5. The process according to claim 4 wherein the weight ratio of said benzene to said heavy polyalkylated aromatic compound containing stream is between 25:1 to 50:1.

6. The process according to claim 1 wherein the reactor temperature of said transalkylation is between 190 and 230° C.

7. The process according to claim 1 wherein said heavy polyalkylated aromatic compound mixture comprises 1,1 di-phenyl ethane, bibenzyl, penta-ethylbenzene, phenyl-ethylphenyl-ethanes, hexaethyl-benzene and diethyl-phenyl-ethane.

8. An integrated process for the production of ethylbenzene comprising the steps of:

(A) contacting a molar excess of benzene with ethylene in a distillation column reactor containing a fixed bed molecular sieve characterized as acidic catalytic distillation structure in a distillation reaction zone, thereby concurrently:
(i) catalytically reacting said benzene and ethylene to form alkylation product comprising ethyl benzene and polyalkylated benzene,
(ii) withdrawing said alkylation product at a point below said fixed bed, and
(iii) withdrawing unreacted benzene at a point above said fixed bed;

(B) fractionating said withdrawn alkylation product;

(C) recovering ethylbenzene as a product from said fractionation;

(D) recovering polyalkylated benzenes as bottoms from said fractionation;

(E) further fractionating said bottoms to separate polyethylbenzenes from heavier polyalkylated benzenes;

(F) contacting said polyethylbenzenes and benzene in liquid phase with a fixed bed acidic zeolite catalyst in a first transalkylation reactor to transalkylate said polyethylbenzenes to ethyl benzene;

(G) recovering a transalkylated product comprising ethyl benzene;

(H) fractionating said transalkylated product to separate ethylbenzene therefrom;

(I) contacting said heavier polyalkylated benzenes and benzene in at least partial liquid phase with a fixed bed acidic zeolite catalyst in a second transalkylation reactor to convert a portion of said heavier polyalkylated benzene to ethylbenzene and polyethylbenzenes;

(J) fractionating the effluent from said second transalkylation reactor to recover unreacted benzene and the ethylbenzene and polyethylbenzenes contained therein; and (K) feeding said recovered benzene and said ethylbenzene and polyethylbenzenes from step (J) to said distillation column reactor.

9. The process according to claim 8 wherein a portion of said recovered benzene and said ethylbenzene and polyethylbenzenes from step (J) is fed to said first transalkylation reactor.

10. In a process for the alkylation of benzene with propylene comprising reacting propylene with a benzene to produce a reaction mixture of cumene and poly-alkylated benzene, separating cumene and a polyisopropyl benzene mixture containing tetraisopropyl benzene and lighter polyalkylated aromatic compounds, and recovering a polyalkylated aromatic compound mixture, containing polyalkylated aromatic compounds heavier than tetraisopropyl benzene, wherein the improvement comprises reacting said polyalkylated aromatic compound mixture with said benzene in the presence of a transalkylation catalyst under transalkylation conditions to produce cumene and a polyalkylated aromatic compound mixture containing tetraisopropyl benzenes and lighter polyalkylated aromatic compounds.

11. The process according to claim 10 wherein said transalkylation catalyst comprises acidic zeolite.

12. The process according to claim 11 wherein said transalkylation catalyst comprises Y zeolite.

13. The process according to claim 10 wherein the weight ratio of said benzene to said heavy polyalkylated aromatic compound containing stream is between 2:1 to 100:1.

14. The process according to claim 13 wherein the weight ratio of said benzene to said heavy polyalkylated aromatic compound containing stream is between 25:1 to 50:1.

15. The process according to claim 10 wherein the reactor temperature of said transalkylation is between 190–230° C.

16. An integrated process for the production of cumene comprising the steps of:
 (A) contacting a molar excess of benzene with propylene in a distillation column reactor containing a fixed bed molecular sieve characterized as acidic catalytic distillation structure in a distillation reaction zone, thereby concurrently:
  (i) catalytically reacting said benzene and propylene to form alkylation product comprising cumene and polyalkylated benzene,
  (ii) withdrawing said alkylation product at a point below said fixed bed, and
  (iii) withdrawing unreacted benzene at a point above said fixed bed;
 (B) fractionating said withdrawn alkylation product;
 (C) recovering cumene as a product from said fractionation;
 (D) recovering polyalkylated benzenes as bottoms from said fractionation;
 (E) further fractionating said bottoms to separate polyisopropylbenzenes from heavier polyalkylated benzenes;
 (F) contacting said polyisopropylbenzenes and benzene in liquid phase with a fixed bed acidic zeolite catalyst in a first transalkylation reactor to transalkylate said polyisopropylbenzenes to cumene;
 (G) recovering a transalkylated product comprising cumene;
 (H) fractionating said transalkylated product to separate cumene therefrom;
 (I) contacting said heavier polyalkylated benzenes and benzene in at least partial liquid phase with a fixed bed acidic zeolite catalyst in a second transalkylation reactor to convert a portion of said heavier polyalkylated benzene to cumene and polyisopropylbenzenes;
 (J) fractionating the effluent from said second transalkylation reactor to recover unreacted benzene and the cumene and polyisopropylbenzenes contained therein; and
 (K) feeding said recovered benzene and said cumene and polyisopropylbenzenes from step (J) to said distillation column reactor.

17. The process according to claim 16 wherein a portion of said recovered benzene and said cumene and polyisopropylbenzene from step (J) is fed to said first transalkylation reactor.

* * * * *